United States Patent
Perry

(10) Patent No.: US 12,410,388 B2
(45) Date of Patent: *Sep. 9, 2025

(54) PHOTOBIOREACTOR SYSTEMS AND METHODS

(71) Applicant: Blue Evolution Inc., Los Altos, CA (US)

(72) Inventor: Beau G. Perry, San Francisco, CA (US)

(73) Assignee: Blue Evolution Inc., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/228,416

(22) Filed: Jul. 31, 2023

(65) Prior Publication Data

US 2023/0407218 A1 Dec. 21, 2023

Related U.S. Application Data

(63) Continuation of application No. 17/564,779, filed on Dec. 29, 2021, now Pat. No. 11,866,681.
(Continued)

(51) Int. Cl.
*C12M 1/00* (2006.01)
*A01G 7/04* (2006.01)
(Continued)

(52) U.S. Cl.
CPC ............ *C12M 21/02* (2013.01); *A01G 7/045* (2013.01); *A01G 33/00* (2013.01); *C12M 23/46* (2013.01);
(Continued)

(58) Field of Classification Search
CPC ...... C12M 21/02; C12M 29/00; C12M 41/48; A01G 33/00; C12N 5/04
See application file for complete search history.

(56) References Cited

U.S. PATENT DOCUMENTS 6,670,169 B1 12/2003 Schob et al.
8,658,420 B2 2/2014 Gorny et al.
(Continued)

FOREIGN PATENT DOCUMENTS

CL 2014002744 A1 4/2015
CL 2023003008 A1 5/2024
(Continued)

OTHER PUBLICATIONS

English machine translation of CN-110257227-A. Translated on Nov. 22, 2022.
(Continued)

*Primary Examiner* — Liban M Hassan
(74) *Attorney, Agent, or Firm* — ArentFox Schiff LLP; Shawn P. Foley; Gabriel L. Hendricks

(57) ABSTRACT

A photobioreactor including a containment structure containing a liquid culture medium for cultivating seaweed. The containment structure includes a sidewall extending vertically between a top and bottom section where the bottom section has an effluent arranged to allow extraction of cultivated seaweed. A spiral liner is positioned adjacent to an inside surface of the sidewall. Light emitters are arranged along a surface of the spiral liner. Flow generators, positioned within the containment structure in a spiral configuration between the top section and bottom section, are configured to direct a flow of the liquid culture medium from the top section toward the bottom section of the containment structure.

19 Claims, 5 Drawing Sheets

Related U.S. Application Data

(60) Provisional application No. 63/172,407, filed on Apr. 8, 2021.

(51) Int. Cl.
  *A01G 33/00* (2006.01)
  *C12M 1/36* (2006.01)
  *C12M 3/00* (2006.01)
  *C12N 5/04* (2006.01)

(52) U.S. Cl.
  CPC ............ *C12M 29/00* (2013.01); *C12M 41/48* (2013.01); *C12N 5/04* (2013.01)

(56) References Cited

U.S. PATENT DOCUMENTS

| | | |
|---|---|---|
| 8,895,279 B2 | 11/2014 | Burke |
| 9,376,656 B2 | 6/2016 | Bartilson |
| 9,816,065 B2 | 11/2017 | Kramer et al. |
| 9,938,492 B2 | 4/2018 | Gressel et al. |
| 10,407,653 B2 | 9/2019 | Auner et al. |
| 2009/0130706 A1 | 5/2009 | Berzin et al. |
| 2010/0216203 A1 | 8/2010 | Trent et al. |
| 2011/0129906 A1 | 6/2011 | Edelson |
| 2015/0143806 A1 | 5/2015 | Friesth |
| 2018/0119083 A1 | 5/2018 | Zheng et al. |
| 2020/0100447 A1 | 4/2020 | Shoham et al. |

FOREIGN PATENT DOCUMENTS

| | | |
|---|---|---|
| CL | 2023003009 A1 | 5/2024 |
| CN | 201245657 Y | 5/2009 |
| CN | 109749916 A | 5/2019 |
| CN | 110257227 A | 9/2019 |
| EP | 2360235 A1 | 8/2011 |
| EP | 3659431 A1 | 6/2020 |
| ES | 2652250 T3 | 2/2018 |
| FR | 2646989 A1 | 11/1990 |
| GB | 2469198 A | 10/2010 |
| IN | 102134553 A | 7/2011 |
| IT | 201900000355 A1 | 7/2020 |
| JP | S60-126075 A | 7/1985 |
| JP | 2015039316 A | 3/2015 |
| KR | 1020170073915 A | 6/2017 |
| WO | 2007011343 A1 | 1/2007 |
| WO | 2010/053394 A1 | 5/2010 |
| WO | 2010/103154 A2 | 9/2010 |
| WO | 2013153402 A1 | 10/2013 |
| WO | 2016123077 A1 | 8/2016 |
| WO | 2017051334 A1 | 3/2017 |
| WO | 2020161711 A1 | 8/2020 |

OTHER PUBLICATIONS

Nagase et al, "English machine translation of JP 2015-039316 A".
Nam et al., "English machine translation of KR20170073915A".
English machine translation of ES2652250T3. Translated on Nov. 9, 2022.
International Search Report and Written Opinion in Application No. PCT/US2022/020529 dated Oct. 13, 2022, 9 pages.
International Search Report and Written Opinion in Application No. PCT/US2022/020530 dated Oct. 13, 2022, 10 pages.

PHOTOBIOREACTOR SYSTEMS AND METHODS

REFERENCE TO RELATED APPLICATIONS

This application is a continuation application of U.S. patent application Ser. No. 17/564,779, filed on Dec. 29, 2021, which claims priority to and the benefit of U.S. Provisional Patent Application No. 63/172,407, filed on Apr. 8, 2021, entitled "PHOTOBIOREACTOR SYSTEMS AND METHODS." The entire contents of the above-referenced applications are incorporated herein by reference.

TECHNICAL FIELD

This application relates generally to photobioreactors and, more particularly, to photobioreactors for algae and seaweed cultivation, useful for carbon sequestration, biomaterials and biofuels production.

BACKGROUND

Bioreactors are systems that promote a biologically active environment. A typical bioreactor has a vessel where a chemical process is carried out involving organisms or biochemically active substances derived from organisms. Some common bioreactors have a cylindrical shape. Bioreactors typically operate in one of several modes including a batch, fed batch, or continuous mode, such as continuous stirred-tank bioreactors. Organisms growing in bioreactors are usually submerged in a liquid such as water or sea water. Environmental conditions inside a bioreactor such as temperature, nutrient concentrations. pH, dissolved gases, and light intensity can be controlled. A photobioreactor (PBR) is a type of bioreactor that uses natural or artificial light to enhance the chemical process within the bioreactor. Photobioreactors are often used to grow phototrophic organisms including cyanobacteria, algae, or moss plants. Seaweeds are a group of algae. All seaweed species are autotrophic while some algae species rely on other external food materials. Light provides an energy source via photosynthesis to organisms that can eliminate the need for sugars or lipids as an energy source.

Algae or seaweed biomass produced by a bioreactor can be dried and used as a food for humans. Derived fine biochemical products can be extracted from algae including, for example, cosmetic pigments, fatty acids, antioxidants, proteins with prophylactic action, growth factors, antibiotics, vitamins and polysaccharides. An algae biomass is also useful, in a low dose, to replace or decrease the level of antibiotic in animal food or can be useful as a source of proteins. An algae biomass in wet form can be fermented or liquefied by a thermal process to produce a biofuel. Early photobioreactors used shallow lagoons agitated with one or several paddle wheels. These photobioreactors had poor productivity and were susceptible to seasonal and daily climate variations. They were also confined to tropical and subtropical areas and prone to contamination. Closed cultivating systems address limitations associated with shallow lagoon or open systems by providing more consistent control of environmental conditions such as light, temperature, and culture mixture within the bioreactor. Some bioreactors inject inorganic carbon in the form of gaseous $CO_2$ or bicarbonate as a source of carbon to enhance the growth of microalgae.

Unfortunately, there remains a need for improved algae and seaweed cultivation to increase the quality, efficiency, diversity, and output yield of algae and seaweed producing bioreactors.

SUMMARY

The application, in various implementations, addresses deficiencies associated with cultivating algae and/or seaweed using photobioreactors. This application describes exemplary photobioreactor systems, methods, and devices that more effectively and efficiently cultivate algae and/or seaweed by configuring a bioreactor to optimally stimulate biomass production and/or yield. The optimization may be enhanced by unique arrangement of flow generators and/or light emitters within the bioreactor. The optimization may be enhanced by monitoring environmental conditions using sensors to provide sensor data to a bioreactor controller that uses artificial intelligence (AI) and/or machine learning (ML) to process the sensor data while dynamically adjusting operations of various bioreactor components to adjust one or more environment conditions within the bioreactor and, thereby, optimize biomass quality and/or yield or optimize seaweed characteristics for a targeted use. There is an increased need for large scale global seaweed production especially focused on sustainable protein and carbon neutral energy to meet the needs of a climate challenged world. The efficiencies and associated technologies of this application are needed to address the needs of an increased population. A new type of photobioreactor is proposed to address these unique marketplace challenges.

In one aspect, a photobioreactor includes a containment structure arranged to contain a liquid culture medium for cultivating seaweed. The liquid culture medium may include seawater, nutrients, and/or seaweed. The containment structure includes at least one sidewall extending vertically between a top and bottom section. The structure may have a cylindrical, silo, rectangular, square, and/or other geometric shape. The bottom section may include an effluent portal arranged to allow extraction of cultivated seaweed. The bioreactor includes a spiral liner positioned adjacent to an inside surface of the at least one sidewall and is in contact with the liquid culture medium. The bioreactor may also include a recirculator having an inlet proximate to the bottom section and outlet proximate to the top section of the containment structure.

The recirculator includes a pump arranged to continuously receive a portion of the liquid culture medium via the inlet from the bottom section and output the portion of the liquid culture medium via the outlet proximate to the top section. The bioreactor further includes an array of sensors arranged to monitor at least one environmental condition within the bioreactor. The bioreactor includes an array of light emitters arranged adjacent to a surface of the spiral liner and/or along a spiral conduit. The bioreactor also includes a plurality of flow generators, positioned within the containment structure in a spiral configuration between the top section and bottom section, arranged to direct a flow of the liquid culture medium from the top section toward the bottom section of the containment structure along a downward spiral path. In some implementations, one or more light emitters or a portion of the array of light emitters is arranged along the downward spiral path to enhance the transmission of light energy to a seaweed biomass traveling along the downward path.

An environmental condition may include a biomass flow rate, temperature, nutrient concentrations, pH levels, dissolved gas concentrations, or light intensity within the liquid culture medium. In one implementation, the array of light emitters includes light emitting diodes (LEDs). In some configurations, the recirculator includes a medium return system forming a channel within the containment structure including an inlet proximate to the bottom section and outlet proximate to the top section. The medium return system includes a pump arranged to continuously receive a portion of the liquid culture medium via the inlet from the bottom section of the containment structure and output the portion of the liquid culture medium via the outlet to the top section of the containment structure. In some implementations, a flow generator includes an eductor.

The photobioreactor may include a controller arranged to receive sensor data from an array of sensors based on one or more environmental condition monitored within the photobioreactor. The controller may adjust flow rate, temperature, nutrient concentrations, pH levels, dissolved gas concentrations, and/or light intensity within the liquid culture medium. The controller may adjust environmental conditions by opening, closing, turning on, turning off, adjusting flow rate, and/or adjusting mixing rate of one or more components of the photobioreator and/or adjusting light intensity of light emitters of the photobioreactor.

The controller may implement artificial intelligence, machine learning, and/or deep learning to optimize predictive analytics for quality control monitoring and/or seaweed production optimization. A portion of the sensors may use a data network, e.g. Internet-of-Things (IoT), in proximity to the photobioreactor and other photobioreactors to generate real-time sensor data via a cloud computing network. The real-time sensor data may be receivable by the controller, one or more offsite control systems, and/or one or more remote monitoring systems. The photobioreactor and the other photobioreactors may be communicatively coupled to form a biorefinery network. The controller, one or more offsite control systems, and/or one or more monitoring systems may be arranged to perform robotic process automation (RPA) to facilitate automation of sensor data collection, testing, maintenance, and/or harvesting of seaweed at one or more photobioreactors.

Any two or more of the features described in this specification, including in this summary section, may be combined to form implementations not specifically described in this specification. Furthermore, while this specification may refer to examples of systems, methods, and devices related algae or seaweed producing bioreactors, such techniques also apply equally to bioreactors arranged to cultivate other organisms. For example, the systems and methods described herein related to photobioreactors can be used for any kind of aquaculture such as, without limitation, crustaceans, fish, mollusks, echinoderms, and the like.

The details of one or more implementations are set forth in the accompanying drawings and the following description. Other features and advantages will be apparent from the description and drawings, and from the claims.

DESCRIPTION OF THE DRAWINGS

Like reference numerals in different figures indicate like elements.

DETAILED DESCRIPTION

The application, in various implementations, addresses deficiencies associated with cultivating algae and/or seaweed using bioreactors. This application describes exemplary systems, methods, and devices that effectively and efficiently implement algae and/or seaweed cultivation by configuring a photobioreactor to optimally stimulate biomass production and/or yield. The optimization may be enhanced by a particular arrangement of flow generators and/or light emitters within the bioreactor. The optimization may be further enhanced by monitoring environmental conditions using sensors to provide sensor data to a bioreactor controller that uses AI and/or ML to process the sensor data and dynamically adjust operations of various bioreactor components to adjust one or more environment conditions within the bioreactor, which optimizes biomass quality and/or yield, or optimizes seaweed characteristics for a targeted use.

Figure 1:
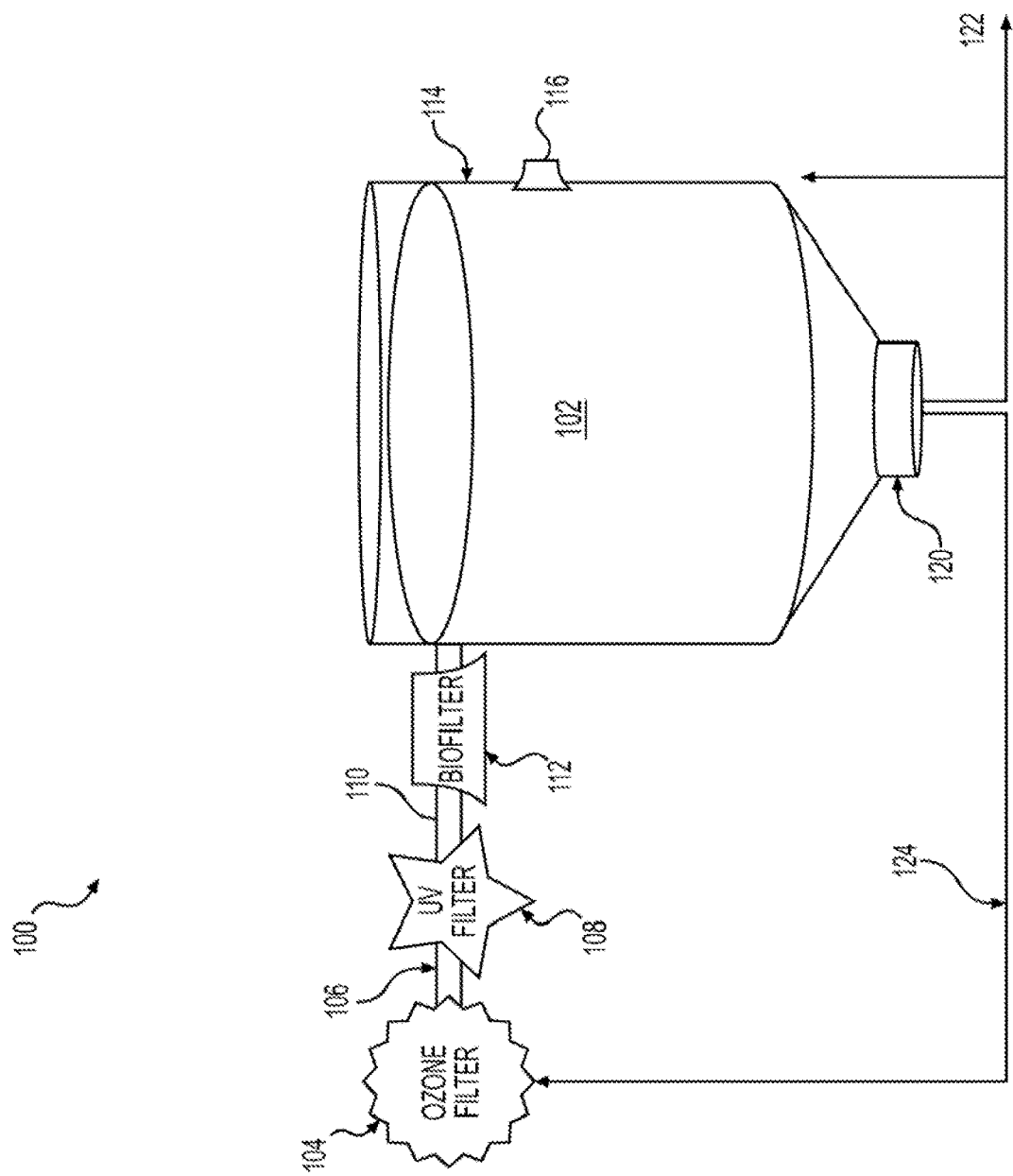
FIG. 1 is a diagram of an exemplary photobioreactor.

FIG. 1 is a diagram of an exemplary of a photobioreactor 100 including a containment structure, vessel, and/or housing 102. Bioreactor 100 also includes a recirculator 124 connected to a seawater intake 110 having an ozone filter 104, $CO_2$ injector 106, Ultraviolet (UV) filter 108, and biofilter 112. Recirculator 124 and seawater intake 110 provide an input of seawater into containment structure 102 proximate to a top section of structure 102. Seawater intake 110 and/or a dedicated nutrient injector 114 may provide nutrients to a liquid medium, e.g., seawater with or without nutrients, in structure 102. Seawater intake 110 and/or recirculator 124 may use one or more mixing educators to mix liquids from the recirculated liquid from the bioreactor, seawater, nutrients, and other inputs into the containment structure 102. Bioreactor 100 may include one or more environment sensors and/or an array of sensors 116 arranged to sense one or more environmental conditions within bioreactor 100. Bioreactor 100 includes a harvester 122 arranged to strain seaweed biomass from outgoing water at effluent portal 120 and either reduce the seawater biomass in size that is recirculated back into the containment structure 102 or harvest out a portion of the seawater biomass.

Figure 3:
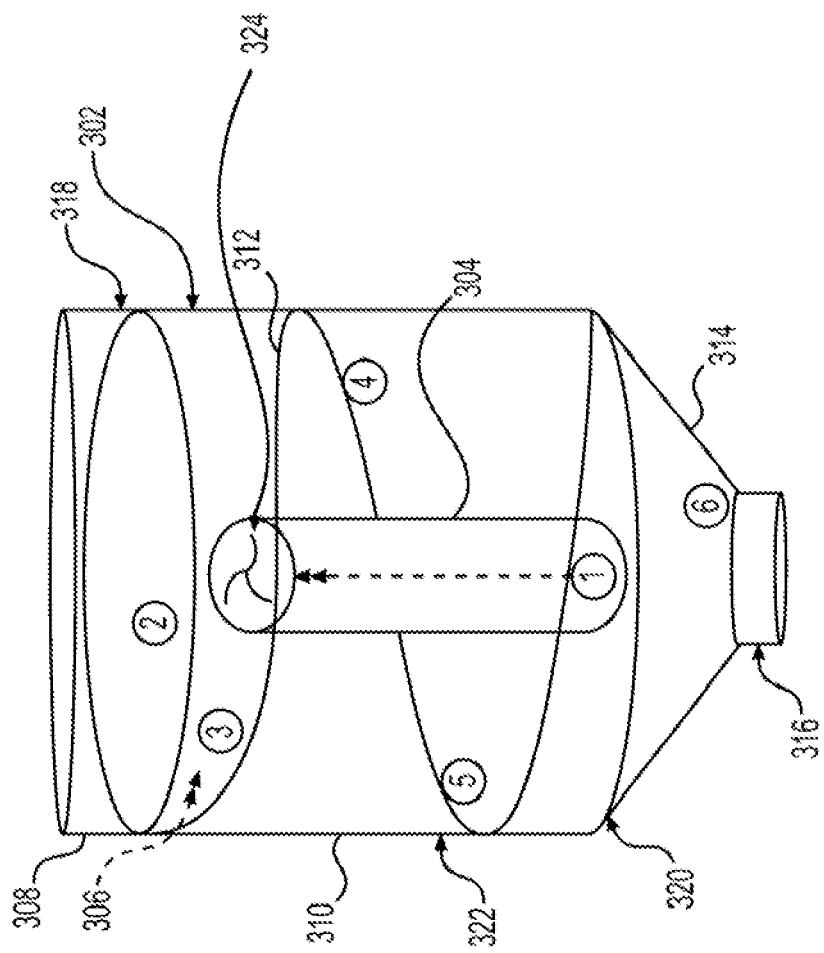
FIG. 3 shows a side view of a photobioreactor.
Figure 4:
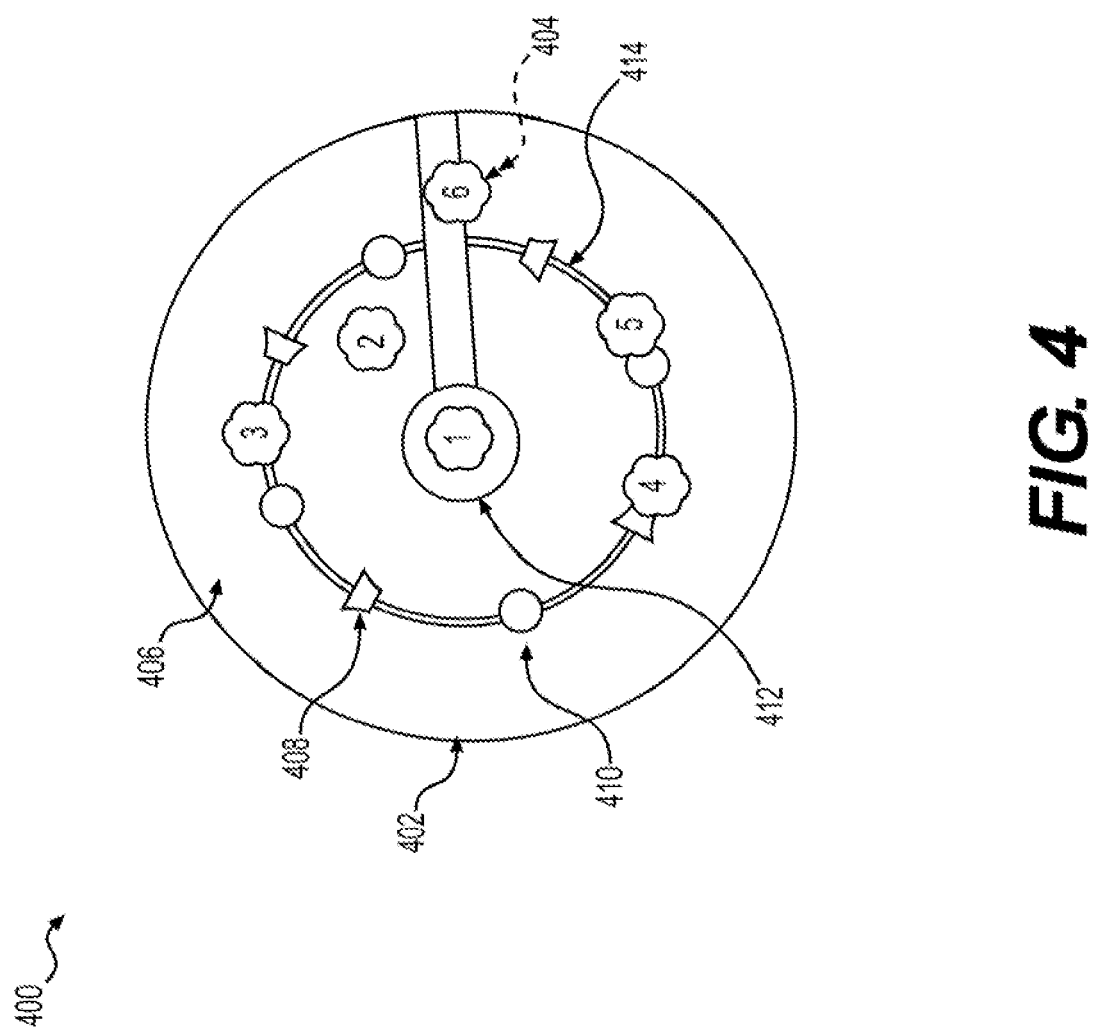
FIG. 4 shows a top-down view of the photobioreactor of FIG. 3.

In some implementations, bioreactor 100 includes a spiral liner positioned adjacent to an inside surface of the at least one sidewall and which is in contact with the liquid culture medium, such as disclosed with respect to FIGS. 3 and 4. In some implementations, bioreactor 100 includes a plurality of flow generators as described with respect to FIGS. 3 and 4, positioned within containment structure 102 in a spiral configuration between the top section and bottom section, arranged to direct a flow of the liquid culture medium from the top section toward the bottom section of containment structure 102.

In certain implementations, bioreactor 100 includes a controller 118 arranged to enable automated control of components of bioreactor 100. Controller 118 may include a processor running artificial intelligence (AI) and/or machine learning (ML), neural networks, Bayesian networks, and/or fuzzy logic to process sensor data received from sensor array 116 and control various environmental parameters of bioreactor 100 including, without limitation, biomass flow rates, temperature, nutrient concentrations, pH levels, dissolved gases concentrations, and/or light intensity. Controller 118 may implement Artificial Neural Networks (ANN) and/or Deep-learning architectures such as deep neural networks, deep belief networks, recurrent neural networks and convolutional neural networks to dynamically adjust environmental conditions within bioreactor 100 or 300. Controller 118 may implement supervised learning, reinforcement learning, and/or unsupervised learning. Reinforced learning may include game theory, control theory, operations research, information theory, and/or simulation-based optimization to dynamically adjust environmental conditions within bioreactor 100 or 300. The bioreactor cultivation environment may be represented as a Markov decision process (MDP). Controller 118 may create multiple decision trees that solve multiple cultivation optimization problems. Controller 118 may use Bayesian networks to optimize an algae and/or seaweed cultivation process.

Controller 118 may use one or more neural networks, such multilayer perceptrons (MLPs), convolutional neural networks (CNNs), or deep Boltzman machines (DBM) that are trained to compute a function that maps an input vector to an output vector. The N-element output vector may convey estimates of the probabilities of N cultivation settings. In some implementations, controller 118 uses a recurrent neural network (RNN) where its neurons send feedback signals to each other to enable dynamic temporal behavior. Controller 118 may use an enhanced RNN referred to as long short-term memory (LSTM) and/or hierarchal temporal memory (HTM). Controller 118 may use a combination of the aforementioned AI algorithms to form a hybrid control system. A decision tree is a generic term that describes a decision process that may use one or more attributes at each node and/or use an information theoretic measure to formulate queries at each node to reach a decision on the optimal cultivation configuration for growing algae and/or seaweed in bioreactor 100.

In operation in one implementation, seaweed and seawater are pumped up through recirculator 124 to top section of containment structure 102. e.g., the top of the liquid culture medium and/or water column. Seaweed reaches surface and begins to sink and spiral back down through the containment structure 102. Seaweed travels along a layer of textile liner while spinning down inside the containment structure and/or silo 102. Seaweed is simultaneously pushed through a spiral conduit and "rotated" by one or more flow generators, e.g, eductors, plumbed into the spiral. Seaweed is exposed to spectrally tuned LED light emitted from light emitters to support or enhance cultivation and/or growth. Heavier biomass and/or other solids are selected out via a vortex of effluent portal 120 for harvest and/or size reduction and/or removal, whereby smaller and/or lighter biomass is sucked into recirculator 124 and pumped back to the top section of containment structure 102. The above cycle repeats continuously during operation.

The diameter or distance between two sidewalls of bioreactor 100 or 300 may be greater than or equal to 0.5 m, 1 m, 2 m, 3 m, 5 m, 7 m, 10 m, 15 m, 20 m, 30 m, 40 m, or 50 meters. The depth or distance from top to bottom of bioreactor 100 or 300 may be greater than or equal to 0.5 m, 1 m, 2 m, 3 m, 5 m, 7 m, 10 m, 15 m, 20 m, 30 m, 40 m, or 50 meters. The containment structure 102 and/or bioreactor 100 may be partially or fully mounted below a ground surface. The containment structure 102 and/or bioreactor 100 may be partially or fully mounted above a ground surface to facilitate more efficient harvesting of biomass, Two or more bioreactors 100 and/or an array of bioreactors 100 may be mounted adjacent to each other to facilitate more efficient biomass harvesting and/or production. The containment structure 102 and/or bioreactor 100 may be partially or fully mounted within a body of water. The containment structure 102 and/or bioreactor 100 may be partially or fully mounted within a body of water periodically, at certain times of day, or during certain tidal events. Light emitters within containment structure 102 may be equally spaced apart horizontally, vertically, and/or circumferentially. Flow generators within containment structure 102 may be equally spaced apart horizontally, vertically, and/or circumferentially. Containment structure 102 may be formed with and/or contain material such as, without limitation, metal (e.g., steel), plastic, concrete, and/or earth materials.

By facilitating a flow of biomass in a downward spiral formation and/or flow path within containment structure 102, bioreactor 100 enables more accurate and efficient detection and/or measurement of biomass flow, volume, and/or yield at a given time or period of time. Bioreactor 100 may include at least one video sensor within containment structure 102. The video sensor may be configured to measure one or more characteristics of the biomass as it flow past the sensors field of view. The video sensor may provide sensor data to enable a determination and/or detection by, for example, controller 118 of biomass density, distribution, flow, foreign material and/or invasive species. In some configurations, bioreactor 100 includes multiple video sensors positioned along the spiral flow path of the biomass within containment structure 102.

In various implementations, bioreactor 100 operates as a closed and/or on-shore bioreactor. There a numerous advantages to operating an on-shore bioreactor including enhanced climate control, control of chemical properties of the liquid culture medium such as nutrient concentrations, and cultivation of types of seaweed tailored for higher value markets. For instance, environmental conditions (e.g., protein and/or sugar concentration) can be adjusted to tailor a seaweed product to a particular use such as for human food, biofuel, animal feed, packaging products, and so on.

Figure 2:
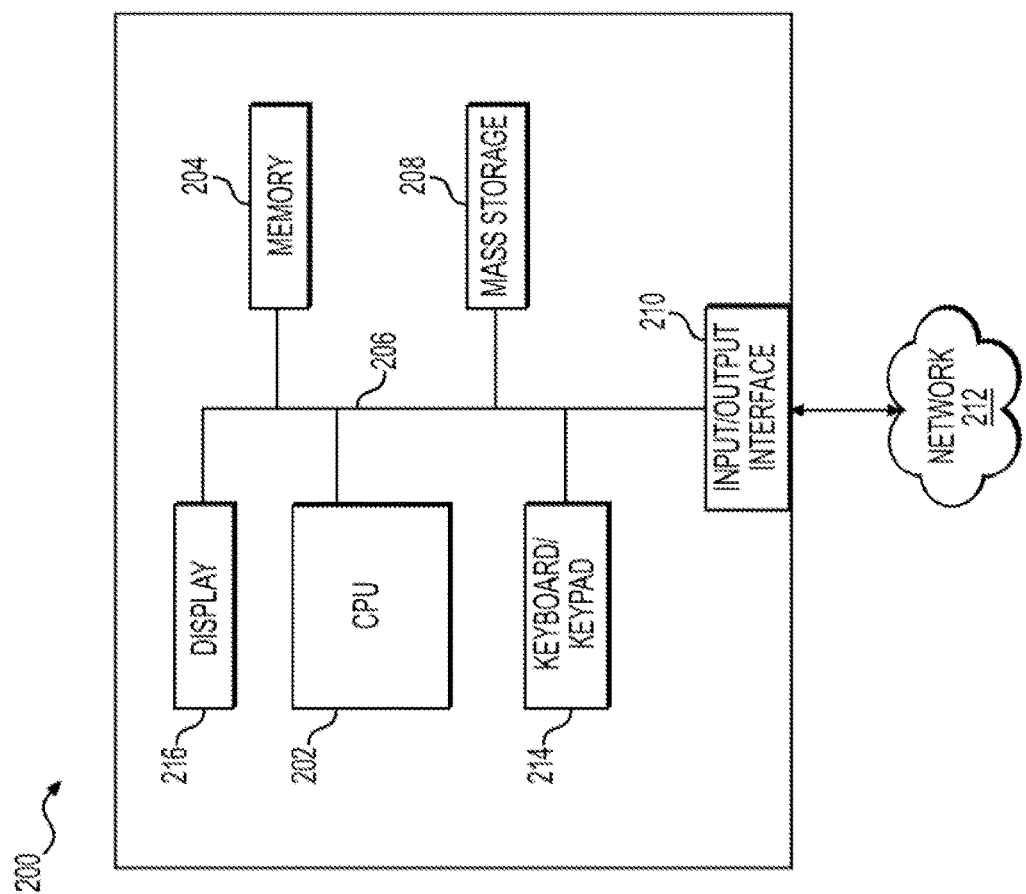
FIG. 2 shows a diagram of a computer system.

FIG. 2 includes a block diagram of a computer system 200 for performing the functions of a computer such as for the controller 118 of FIG. 1. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives or solid state memory, for storing data and instructions for use by the CPU 202. At least one component of the mass storage system 208, preferably in the form of a disk drive, solid state, or tape drive, stores the database used for processing sensor data from sensor array 116 and running AI and/or ML engines and/or neural networks for controlling bioreactor 100 or 300. The AI and/or ML engines may implement ANNs and/or Deep-learning architectures such as deep neural networks, deep belief networks, recurrent neural networks and convolutional neural networks to dynamically adjust environmental conditions within bioreactor 100 or 300. To effect automated control of bioreactor 100 or 300, computer 200 may send sensor control signals to various components 104, 106, 108, 110, 112, 114, 120, and 122 of bioreactor 100 or 300 to either, open, close, turn on, turn off, adjust flow rate, adjust mixing rate, and/or light intensity of light emitters, to optimize algae and/or seaweed production within bioreactor 100 or 300. The mass storage system 208 may also include one or more drives for various portable media, such as a floppy disk, flash drive, a compact disc read only memory (CD-ROM, DVD, CD-RW, and variants), memory stick, or an integrated circuit non-volatile memory adapter (i.e. PC-MCIA adapter) to input an d output data and code to and from the computer system 200. In some implementations, computer 200 and/or controller 118 may control multiple bioreactors concurrently via a data network such as network 212. Controller 118 may coordinate operations among the multiple bioreactors to optimize output production and/or yield among the multiple bioreactors. Network 212 may include a wireless, Adhoc, and/or mobile network, supporting multiple computing servers implementation a cloud computing environment. Various environmental sensors and/or multiple bioreactors may be communicatively connected via network 212 as, for example, Internet-of-Things (IoT) capable systems and/or devices. In some implementations, network 212 may enable computer 200 and/or controller 118 to coordinate operations of multiple photobioreactors by using predictive analytics to process, for example, global position system (GPS) data and other big data to coordinate operations and control of multiple concurrently operating bioreactors over a geographic area. In certain implementations, network 212 may enable collections of, for example, GPS data from multiple bioreactors and use an ML program to enhance security and/or performance for seaweed production on land or in the sea.

The computer system 200 may also include one or more input/output interfaces for communications, shown by way of example, as interface 210 and/or transceiver for data communications via the network 212. The data interface 210 may be a modem, an Ethernet card or any other suitable data communications device. To provide the functions of a computer 102, the data interface 210 may provide a relatively high-speed link to a network 212, such as an intranet, or the Internet, either directly or through another external interface. The communication link to the network 212 may be, for example, optical, wired, or wireless (e.g., via satellite or cellular network). Alternatively, the computer system 200 may include a mainframe or other type of host computer system capable of Web-based communications via the network 212. The computer system 200 may include software for operating a network application such as a web server and/or web client.

The computer system 200 may also include suitable input/output ports, that may interface with a portable data storage device, or use the interconnect bus 206 for interconnection with a local display 216 and keyboard 214 or the like serving as a local user interface for programming and/or data retrieval purposes. The display 216 and/or display 120 may include a touch screen capability to enable users to interface with the system 200 by touching portions of the surface of the display 216. Remote operations personnel may interact with the system 200 for controlling and/or programming the system from remote terminal devices via the network 212.

The computer system 200 may run a variety of application programs and store associated data in a database of mass storage system 208. One or more such applications may include a bioreactor controller 118 that controls various components of system 100 or 300 during the algae and/or seaweed cultivation and/or growth process.

The components contained in the computer system 200 may enable the computer system to be used as a server, workstation, personal computer, network terminal, mobile computing device, and the like. As discussed above, the computer system 200 may include one or more applications that enable cleaning and sanitization of a footwear sole or soles. The system 200 may include software and/or hardware that implements a web server application. The web server application may include software such as HTML, XML, WML, SGML, PHP (Hypertext Preprocessor), CGI, and like languages.

The foregoing features of the disclosure may be realized as a software component operating in the system 200 where the system 200 includes UNIX workstation, a Windows workstation, a LINUX workstation, or other type of workstation. Other operating systems may be employed such as, without limitation, Windows, MAC OS, and LINUX. In some aspects, the software can optionally be implemented as a C language computer program, or a computer program written in any high level language including, without limitation, JavaScript, Java, CSS, Python, PHP, Ruby, C++, C, Shell, C#, Objective-C, Go, R, TeX, VimL, Perl, Scala, CoffeeScript, Emacs Lisp, Swift, Fortran, or Visual BASIC. Certain script-based programs may be employed such as XML, WML, PHP, and so on. The system 200 may use a digital signal processor (DSP).

As stated previously, the mass storage 208 may include a database. The database may be any suitable database system, including the commercially available Microsoft Access database, and can be a local or distributed database system. A database system may implement Sybase and/or an SQL Server. The database may be supported by any suitable persistent data memory, such as a hard disk drive, RAID system, tape drive system, floppy diskette, or any other suitable system. The system 200 may include a database that is integrated with the system 200, however, it is understood that, in other implementations, the database and mass storage 208 can be an external element.

In certain implementations, the system 200 may include an Internet browser program and/or to be configured to operate as a web server. In some configurations, the client and/or web server may be configured to recognize and interpret various network protocols that may be used by a client or server program. Commonly used protocols include Hypertext Transfer Protocol (HTTP), File Transfer Protocol (FTP), Telnet, and Secure Sockets Layer (SSL), and Transport Layer Security (TLS), for example. However, new protocols and revisions of existing protocols may be frequently introduced. Thus, in order to support a new or revised protocol, a new revision of the server and/or client application may be continuously developed and released.

The computer system 200 may include a web server running a Web 2.0 application or the like. Web applications running on system 200 may use server-side dynamic content generation mechanisms such, without limitation, Java servlets, CGI, PHP, or ASP. In certain embodiments, mashed content may be generated by a web browser running, for example, client-side scripting including, without limitation, JavaScript and/or applets on a wireless device.

In certain implementations, system 200 and/or controller 118 may include applications that employ asynchronous JavaScript+XML (Ajax) and like technologies that use asynchronous loading and content presentation techniques. These techniques may include, without limitation, XHTML and CSS for style presentation, document object model (DOM) API exposed by a web browser, asynchronous data exchange of XML data, and web browser side scripting, e.g., JavaScript. Certain web-based applications and services may utilize web protocols including, without limitation, the services-orientated access protocol (SOAP) and representational state transfer (REST). REST may utilize HTTP with XML.

The system 200 may also provide enhanced security and data encryption. Enhanced security may include access control, biometric authentication, cryptographic authentication, message integrity checking, encryption, digital rights management services, and/or other like security services. The security may include protocols such as IPSEC and IKE. The encryption may include, without limitation, DES, 3DES, AES, RSA, and any like public key or private key based schemes.

FIG. 3 shows a side view of photobioreactor 300 including a recirculator and/or return system 304 within its containment structure 302. Containment structure 302 forms a cavity in which a liquid culture medium 310, e.g., a seawater growing medium, is contained. Recirculator and/or medium return system 304 forms a channel within containment structure 302 including an inlet proximate to bottom section 320 and outlet proximate to the top section 318. Recirculator 304 includes a pump 324 arranged to continuously receive a portion of liquid culture medium 310 via the inlet in bottom section 320 and output the portion of liquid culture medium 310 via the outlet in top section 318. Recirculator 304 may be position centrally to contribute to a downward spiral flow path 306 of biomass and/or medium 310 within containment structure 302.

Bioreactor 300 also includes a spiral liner 312 adjacent to an inner surface of sidewall 322 of containment structure 302. The spiral liner 312 enables, at least partially, a downward spiral flow path for seaweed 306 from a top section 318 toward a bottom section 320 of containment structure 302. Gravity and/or one or more flow generators may also assist in providing a downward spiral flow of biomass and/or medium 310 within containment structure 302. Bioreactor 300 may also include a vortex grading and draining funnel 314 arranged to enable harvesting of seaweed biomass via effluent portal 316. Containment structure 302 may have a sealed top section 318 arranged to enable a gas layer 308 above the liquid culture medium 310. Although not shown in FIG. 3, bioreactor 300 may include one or more components as described with respect to bioreactor 100 of FIG. 1. For example, bioreactor 300 may include an array of sensors, one or more lights emitters, and/or a controller such as controller 118 of FIG. 1. Bioreactor 300 may be configured to operate as an on-shore and/or closed system or operate as an off-shore and/or open system within a body of water such as the ocean. When operating as an on-shore or closed system, bioreactor 300 may include a recirculator such as recirculator 124 of FIG. 1 in addition to or alternatively to recirculator 304.

FIG. 4 shows a top-down view 400 of photobioreactor 300 of FIG. 3. FIG. 4 includes silo containment structure 402, spiral liner fabric 406, multiple eductors 408, multiple marine light emitters (e.g., LEDs) 410, return column 412 of recirculator 304, and an educator, electrical, and/or drainage conduit 414. FIG. 4 shows a downward spiral flow 404 between return column 412 and spiral liner fabric 406. In certain implementations, flow generators (e.g., eductors 408) and/or light emitters 410 are spaced horizontally, vertically, and/or circumferential equally or substantially equally apart. By arranging multiple light emitters along a vertical depth and/or horizontally at various depths, the vertical length of bioreactors 100 or 300 can be extended substantially with respect to conventional bioreactors that rely on natural sun light. Conventional bioreactors are typically limited to about a 2.5 m depth due to limited penetration of natural light through a cultivating medium via the top of a conventional bioreactor.

By positioning multiple light emitters at various depths and/or along the downward spiral flow path 404 or 306 of medium 310, an exposure of medium 310 to energy provided by light is substantially enhanced to, thereby, increase biomass yield and/or a consistency of the seaweed biomass product. This is another technical advantage of implementing a downward spiral flow path 404 or 306 within bioreactor 300 and/or 100. As discussed with respect to FIG. 1, eductors 408 and/or flow generators may be oriented in a downward direction toward bottom section 320 but also oriented in horizontal direction to encourage the spiral downward flow 404 and 306. In some implementations, eductors 408 and/or flow generators are oriented and/or positioned to promote medium flow 404 and/or 306 in a parallel or substantially parallel direction as spiral liner 312. Eductors 408 may have a vertical orientation less than or equal to 2, 5, 10, 15, 20, 30, or 45 degrees from horizontal in a downward direction toward bottom section 320 and/or effluent portal 316 or 120.

Figure 5:
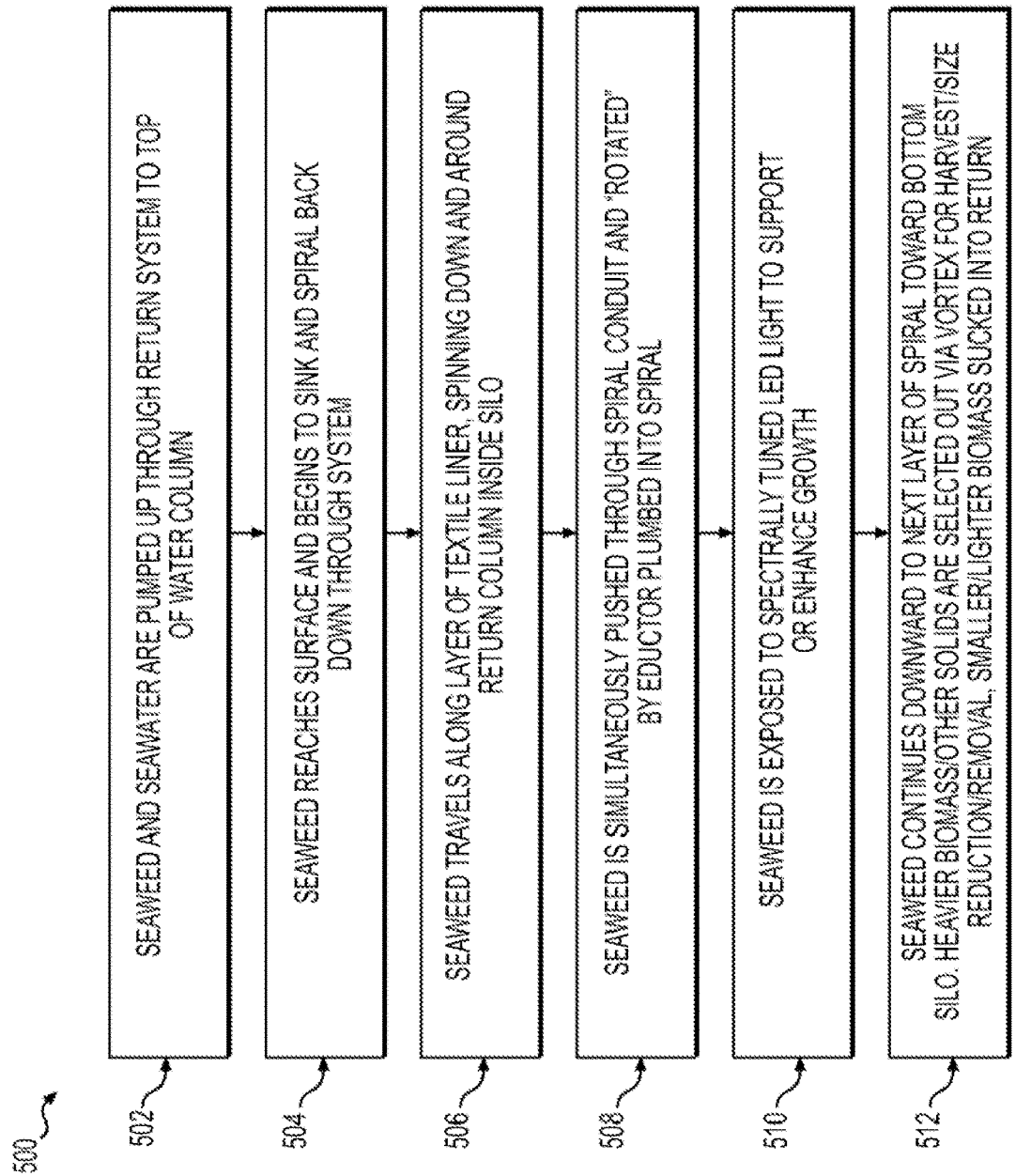
FIG. 5 illustrates a seaweed cultivation process related to the operation of the bioreactor of FIGS. 3 and 4.

FIG. 5 illustrates a seaweed cultivation process 500 related to the operation of photobioreactor 300 of FIGS. 3 and 4. Seaweed and seawater are pumped up through return column 412 and/or recirculator 304 to top section 318 of containment structure 302 and/or 402, e.g., the top of liquid culture medium 310 and/or return column 412 (Step 502 and Item 1 of FIGS. 3 and 4). Seaweed reaches the surface of medium 310 and begins to sink and spiral back down via path 306 and/or 404 through containment structure 302 and/or 402 (Step 504 and Item 2 of FIGS. 3 and 4). Seaweed travels along a layer of textile liner, e.g., spiral liner 312 and/or spiral liner fabric 406 while spinning down inside containment structure and/or silo 302 and/or 402 (Step 506 and Item 3 of FIGS. 3 and 4). Seaweed is simultaneously pushed through spiral conduit 414 and "rotated" by one or more flow generators, e.g, eductors 408, plumbed into spiral conduit 414 (Step 508 and Item 4 of FIGS. 3 and 4). Seaweed is exposed to spectrally tuned LED light emitted from light emitters 410 to support or enhance cultivation and/or growth (Step 510 and Item 5 of FIGS. 3 and 4). Heavier biomass and/or other solids are selected out via vortex 314 adjacent to effluent portal 316 for harvest and/or size reduction and/or removal, whereby smaller and/or lighter biomass is sucked into recirculator 304 and/or return column 412 and pumped back to the top section 318 of containment structure 302 and/or 402. In some implementations, the above cycle of Steps 502 through 512 repeats continuously during operation of bioreactor 300.

Elements or steps of different implementations described may be combined to form other implementations not specifically set forth previously. Elements or steps may be left out of the systems or processes described previously without adversely affecting their operation or the operation of the system in general. Furthermore, various separate elements or steps may be combined into one or more individual elements or steps to perform the functions described in this specification.

Other implementations not specifically described in this specification are also within the scope of the following claims.

What is claimed is:
1. A photobioreactor comprising:
 a containment structure arranged to contain a liquid culture medium for cultivating seaweed, the containment structure including at least one sidewall extending vertically between a top section and a bottom section;

a spiral liner positioned adjacent to an inside surface of the at least one sidewall and being in contact with the liquid culture medium, the spiral liner configured to enable, at least partially, a downward spiral flow path for the liquid culture medium from the top section toward the bottom section of the containment structure;

an array of sensors positioned along the downward spiral flow path configured to monitor at least one environmental condition within the photobioreactor;

a plurality of flow generators, positioned within the containment structure in a spiral configuration between the top section and bottom section along the downward spiral flow path, configured to direct a flow of the liquid culture medium from the top section toward the bottom section of the containment structure along the downward spiral flow path; and an array of light emitters arranged along a surface of the spiral liner adjacent to the downward spiral flow path.

2. The photobioreactor of claim 1 comprising a recirculator including an inlet adjacent to the bottom section and outlet adjacent to the top section, the recirculator arranged to continuously receive a portion of the liquid culture medium via the inlet of the recirculator and output the portion of the liquid culture medium via the outlet of the recirculator.

3. The photobioreactor of claim 1, wherein the at least one environmental condition includes at least one of biomass flow rate, temperature, nutrient concentrations, pH, dissolved gases, and light intensity.

4. The photobioreactor of claim 1, wherein the array of light emitters includes light emitting diodes.

5. The photobioreactor of claim 1, wherein at least one flow generator of the plurality of flow generators includes an eductor.

6. The photobioreactor of claim 1 comprising a controller configured to receive sensor data from the array of sensors based on the at least one environmental condition monitored within the photobioreactor.

7. The photobioreactor of claim 6, wherein the controller adjusts at least one of flow rate, temperature, nutrient concentrations, pH levels, dissolved gas concentrations, and light intensity within the liquid culture medium.

8. The photobioreactor of claim 7, wherein the controller adjusts the at least one environmental condition by at least one of opening, closing, turning on, turning off, adjusting flow rate, adjusting mixing rate of one or more components of the photobioreator and/or adjusting light intensity of light emitters of the photobioreactor.

9. The photobioreactor of claim 8, wherein the controller implements at least one of artificial intelligence, machine learning, and deep learning to optimize predictive analytics for at least one of quality control monitoring and seaweed production optimization.

10. The photobioreactor of claim 6, wherein a portion of the sensors use a data network in proximity to the photobioreactor and at least a second photobioreactor to generate real-time sensor data via a cloud computing network.

11. A method for cultivating a biomass using a photobioreactor comprising:

containing a liquid culture medium for cultivating seaweed using a containment structure, the containment structure including at least one sidewall extending vertically between a top section and bottom section;

positioning a spiral liner adjacent to an inside surface of the at least one sidewall and in contact with the liquid culture medium, the spiral liner configured to enable, at least partially, a downward spiral flow path for the liquid culture medium from the top section toward the bottom section of the containment structure;

receiving, continuously, a portion of the liquid culture medium via an inlet of a recirculator adjacent to the bottom section;

outputting, continuously, the portion of the liquid culture medium via an outlet of the recirculatory adjacent to the top section;

monitoring at least one environmental condition within the photobioreactor via an array of sensors positioned along the downward spiral flow path;

directing a flow of the liquid culture medium downward from the top section toward the bottom section of the containment structure along the downward spiral flow path with a plurality of flow generators, positioned within the containment structure in a spiral configuration between the top section and bottom section along the downward spiral flow path; and positioning an array of light emitters along a surface of the spiral liner adjacent to the downward spiral flow path.

12. The method of claim 11, comprising outputting, continuously, the portion of the liquid culture medium via an outlet of the recirculator adjacent to the top section.

13. The method of claim 11, wherein the at least one environmental condition includes at least one of biomass flow rate, temperature, nutrient concentrations, pH, dissolved gases, and light intensity.

14. The method of claim 11, wherein the array of light emitters includes light emitting diodes.

15. A photobioreactor comprising:

a containment structure arranged to contain a liquid culture medium for cultivating seaweed, the containment structure including at least one sidewall extending vertically between a top and bottom section;

an array of sensors positioned along a downward spiral flow path for the liquid culture medium adjacent to the at least one sidewall from the top section toward the bottom section of the containment structure; the array of sensors configured to monitor at least one environmental condition within the photobioreactor;

a plurality of flow generators, positioned within the containment structure in a spiral configuration between the top section and bottom section along the downward spiral flow path, configured to direct a flow of the liquid culture medium from the top section toward the bottom section of the containment structure along a downward spiral path; and an array of light emitters arranged along a surface of the sidewall adjacent to the downward spiral flow path.

16. The photobioreactor of claim 15 comprising a recirculator including an inlet adjacent to the bottom section and outlet adjacent to the top section, the recirculator arranged to continuously receive a portion of the liquid culture medium via the inlet of the recirculator and output the portion of the liquid culture medium via the outlet of the recirculator.

17. The photobioreactor of claim 15, wherein the at least one environmental condition includes at least one of biomass flow rate, temperature, nutrient concentrations, pH, dissolved gases, and light intensity.

18. The photobioreactor of claim 15, wherein the array of light emitters includes light emitting diodes.

19. The photobioreactor of claim 15, wherein at least one flow generator of the plurality of flow generators includes an eductor.

* * * * *

UNITED STATES PATENT AND TRADEMARK OFFICE
CERTIFICATE OF CORRECTION

PATENT NO. : 12,410,388 B2
APPLICATION NO. : 18/228416
DATED : September 9, 2025
INVENTOR(S) : Beau G. Perry It is certified that error appears in the above-identified patent and that said Letters Patent is hereby corrected as shown below:

In the Specification

In Column 3, Line 24, delete the following text: "components of the photobioreator and/or adjusting light"
Replace with the following text: -- components of the photobioreactor and/or adjusting light --

In Column 4, Line 34, delete the following text: "recirculator 124 may use one or more mixing educators to"
Replace with the following text: -- recirculator 124 may use one or more mixing eductors to --

In Column 8, Lines 2-5, delete the following text: "As discussed above, the computer system 200 may include one or more applications that enable cleaning and sanitization of a footwear sole or soles."

In Column 9, Lines 56-57, delete the following text: "recirculator 304, and an educator, electrical, and/or drainage conduit 414"

Replace with the following text: -- recirculator 304, and an eductor, electrical, and/or drainage conduit 414 --

In the Claims

In Column 11, Lines 45-46, of Claim 8, delete the following text: "one or more components of the photobioreator and/or adjusting light intensity of light"

Replace with the following text: -- one or more components of the photobioreactor and/or adjusting light intensity of light--

Signed and Sealed this
Ninth Day of December, 2025

John A. Squires
*Director of the United States Patent and Trademark Office*

CERTIFICATE OF CORRECTION (continued)
U.S. Pat. No. 12,410,388 B2

In Column 12, Lines 6-8, of Claim 11, delete the following text: "outputting, continuously, the portion of the liquid culture medium via an outlet of the recirculatory adjacent to the top section"

Replace with the following text: -- outputting, continuously, the portion of the liquid culture medium via an outlet of the recirculator adjacent to the top section --